United States Patent [19]
Feliziani et al.

[11] Patent Number: 5,897,535
[45] Date of Patent: * Apr. 27, 1999

[54] NON-CONTAMINATING PROBE AND METHODS OF MAKING AND USING SAME

[75] Inventors: Roberto Feliziani, Pesaro, Italy; Marc L. Jaker, New Brighton, Minn.

[73] Assignee: RTC, Inc., St. Paul, Minn.

[ * ] Notice: This patent is subject to a terminal disclaimer.

[21] Appl. No.: 08/629,108

[22] Filed: Apr. 8, 1996

Related U.S. Application Data

[62] Continuation of application No. 08/384,571, Feb. 6, 1995, Pat. No. 5,531,717, which is a continuation-in-part of application No. 08/157,145, filed as application No. PCT/US92/04727, Jun. 5, 1992, abandoned.

[30] Foreign Application Priority Data

Jun. 7, 1991 [IT] Italy .................. PS910027 U

[51] Int. Cl.⁶ .................................. A61M 25/01
[52] U.S. Cl. .................. 604/271; 604/171; 604/264; 604/54; 604/349
[58] Field of Search .................. 604/271, 171, 604/264, 349, 54, 93–104; 600/29–31; 128/DIG. 25, DIG. 14; 623/1

[56] References Cited

U.S. PATENT DOCUMENTS

| | | | |
|---|---|---|---|
| 3,084,693 | 4/1963 | Cathcart | 604/271 |
| 3,332,424 | 7/1967 | Minteer | 604/271 |
| 3,421,509 | 1/1969 | Fiore | 604/271 |
| 3,583,391 | 6/1971 | Cox | 128/772 |
| 3,850,720 | 11/1974 | Hampson . | |
| 3,866,601 | 2/1975 | Russell . | |
| 4,251,305 | 2/1981 | Becker et al. . | |
| 4,327,735 | 5/1982 | Hampson . | |
| 4,536,179 | 8/1985 | Andersen et al. | 128/DIG. 14 |
| 4,652,259 | 3/1987 | O'Neil . | |
| 4,713,070 | 12/1987 | Mano . | |
| 4,743,258 | 5/1988 | Ikada . | |
| 4,946,440 | 8/1990 | Hall . | |
| 5,376,085 | 12/1994 | Conway et al. . | |
| 5,531,717 | 7/1996 | Roberto et al. . | |

FOREIGN PATENT DOCUMENTS

| | | |
|---|---|---|
| A-247 559 | 5/1987 | European Pat. Off. . |
| A-1958561 | 6/1970 | German Dem. Rep. . |

*Primary Examiner*—Mark Bockelman
*Attorney, Agent, or Firm*—Snell & Wilmer L.L.P.

[57] ABSTRACT

A non-contaminating catheter includes a hollow tube having an axial lumen extending along the length thereof, and an elongated, tubular, flexible membrane disposed within the lumen. The leading end of the membrane is circumferentially folded back over the leading edge of the tube and fixed to a guide assembly. As the catheter is inserted into a patient, the membrane is drawn through the tube and out the leading edge of the tube. Once the catheter is fully inserted, the membrane circumscribes the tube; thus, contact between the tube and the patient is substantially, if not entirely, prevented during insertion of the catheter over the length of the membrane. More particularly, the membrane is laid out as the catheter is urged along the anatomical canal and thus remains interposed between the exterior wall of the catheter and the patient's internal organs (e.g., the urethra). Sliding frictional contact between the catheter tube and the urethral mucosa is inhibited and the passive transportation of pathogens in the lower urinary tract concomitantly prevented. Various methods of making and using the catheter of the present invention are also disclosed.

4 Claims, 3 Drawing Sheets

NON-CONTAMINATING PROBE AND METHODS OF MAKING AND USING SAME

CROSS-REFERENCE TO RELATED APPLICATIONS

This application is a continuation of U.S. Ser. No. 08/384,571 filed Feb. 6, 1995 of the same title now U.S. Pat. No. 5,531,717. U.S. Ser. No. 08/384,571 is a continuation-in-part of U.S. Ser. No. 08/157,145 filed Dec. 12, 1993 now abandoned entitled NON-CONTAMINATING PROBE, a national stage application based on PCT/US92/04727 filed Jun. 5, 1992 of the same title, an international application claiming priority on Italian application no. PS91 U 000027 filed Jun. 7, 1991.

FIELD OF THE INVENTION

The present invention relates, generally, to sterilized medical probes and, more particularly, to an anti-infectious prophylactic probe useful as a urinary catheter.

BACKGROUND OF THE INVENTION

Catheters or probes are used in a number of medical and related applications. For example, a catheter comprising an elongated, flexible, hollow tube may be inserted into a patient's urethral canal to permit withdrawal of fluids from the bladder. Such catheters are typically referred to as urinary drainage catheters, or simply urinary catheters, and are usually inserted into the bladder by way of the urethra.

It has been found that typical urinary catheters, even if sterile when inserted into a patient, tend to contribute to bladder infections Treatment of such infections often involves the use of heavy medication and may lengthen the catheterized patient's hospital stay. It is believed that the insertion of the catheter through the urethral canal into the bladder dislodges or otherwise attracts infectious material, (i.e., pathogens and bacteria which populate the lower urinary tract), due to the frictional forces the catheter exerts on the urethral walls or urethral mucosa resident on the walls. These bacteria are typically present on the male glans or the distal portion of the male's urethra and on the female's urethral meatus. Once dislodged, the infectious material is carried, typically by the leading edge of the catheter, to the internal organ (e.g., bladder), causing infection of the internal organ.

Even if no infectious or pathogenous material is dislodged, the frictional forces exerted on the urethral walls by conventional catheters tend to irritate the urethral mucosa. While the irritation caused by this mechanical trauma exerted during penetration by the catheter is generally temporary, the discomfort experienced by the patient is nonetheless substantial.

These disadvantages are also encountered in other applications in which a probe or catheter is inserted into a body cavity to either drain or inject internal fluids or for other diagnostic procedures. For example, probes used in cystoscopy also may cause attraction of infectious material or irritation to the canal or orifice into which the catheter is inserted.

Other catheters are known which purport to address these problems; for example, the catheters shown in U.S. Pat. No. 3,421,509 issued to Fiore on Dec. 17, 1965; U.S. Pat. No. 3,084,693 issued to Cathcart on Apr. 9, 1963; DE 1958561 issued to American Hospital and published on Jun. 11, 1970; and EP-A-247 559 issued to Sterimed and published on Dec. 2, 1987. While the catheters described in these references purport to address these problems, as will be shown herein, the catheter constructions of these references are medically unacceptable and, in practice, are inferior in performance to or considerably more complex than the catheter of the present invention. Some of the known catheter constructions simply do not work at all.

There thus exists a long-felt need to ameliorate the disadvantages occasioned by use of known medical probes. There is a particular need for a urinary catheter that does not cause infectious material to be carried or otherwise passed to the bladder.

SUMMARY OF THE INVENTION

The present invention provides an anti-infectious, non-contaminating catheter which addresses the aforementioned drawbacks of presently known catheters.

A preferred exemplary embodiment of the present invention provides, inter alia, a hollow tube having an axial lumen extending along the length thereof, and an elongated, flexible tubular membrane comprising polytetrafluoroethylene (PTFE) disposed within the lumen. The membrane is very thin (less than the thickness of a human hair) and very pliable. The leading end of the membrane is circumferentially folded back over the leading edge of the tube such that as the catheter is inserted into a patient, the membrane is drawn through the tube and out the leading edge of the tube. Once the catheter is fully inserted, the membrane circumscribes the tube. Thus, contact between the tube and the patient is substantially, if not entirely, prevented during insertion of the catheter over the length of the membrane contained there within.

More particularly, the non-contaminating catheter of the present invention includes a protective membrane (sheath) comprising modified polytetrafluoroethylene resin or a derivative thereof, which is laid out as the catheter (probe) is urged along an anatomical canal and thus remains interposed between the exterior wall of the catheter and the walls of the canal (e.g., the urethral canal). In accordance with one aspect of the invention, a polyvinyl chloride catheter tube suitably cooperates with the PTFE membrane such that upon insertion of the catheter into an orifice, such as the urethral canal, sliding frictional contact between the catheter and the urethral mucosa over the length of the membrane is inhibited and the passive transportation of pathogens in the lower urinary tract concomitantly prevented.

The apparatus of the present invention thus facilitates insertion of a catheter into a body cavity in a manner which effectively lessens the irritation caused by the frictional forces exerted by typical catheters and inhibits the dragging of certain pathogens to internal organs during the catheterization procedure. Methods of making and using the catheter of the present invention are also disclosed.

BRIEF DESCRIPTION OF THE DRAWINGS

Preferred exemplary embodiments of the present invention will hereinafter be described in conjunction with the appended drawing figures, wherein like numerals denote like elements and.

DETAILED DESCRIPTION OF PREFERRED EXEMPLARY EMBODIMENTS

Figure 1:
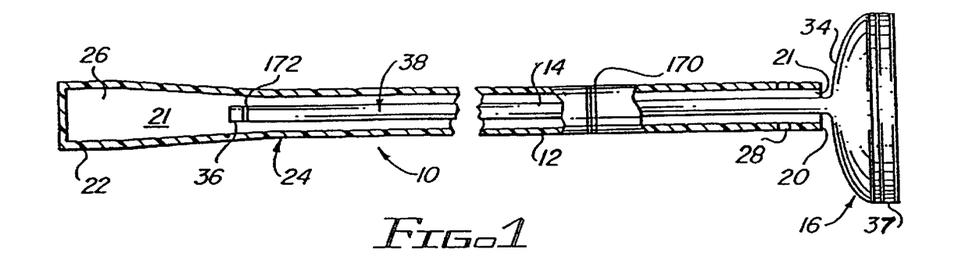
FIG. 1 is a side elevational view of a preferred embodiment of a catheter in accordance with the present invention.

Referring now to FIG. 1, an exemplary non-contaminating catheter 10 in accordance with the present invention preferably includes a catheter tube 12, a membrane (sheath) 14, and a membrane guide ring 16. Membrane 14 suitably comprises a first end 34, a second end 36, and a flexible body 38 spanning therebetween.

A preferred exemplary embodiment of the present invention will be described with reference to catheter 10 as a urinary catheter. It should be appreciated that this description is for purposes of illustration of the invention, and while it describes a preferred embodiment thereof, the invention is not so limited. Various other uses of catheter 10 as are now known or hereafter devised by those skilled in the art are within the scope of the invention. For example, catheter 10 may be used in a variety of other contexts such as a medical probe, a drainage tube, a coronary catheter, and the like.

When catheter 10 is used as a urinary catheter, catheter tube 12 may be of a conventional design and typically includes a leading edge 20, a trailing edge 22, with a generally tubular body 24 and an axial bore (lumen) 21 extending therebetween. As those skilled in the art will appreciate, as a urinary catheter, tube 12 is used to drain fluids from the bladder to a collection reservoir (e.g., a urine collection bag). To that end, tube 12 preferably includes at least one aperture 28 provided in body 24 proximate leading edge 20 of tube 12. In accordance with a particularly preferred aspect of the invention, when catheter 10 is employed as a urinary catheter, two apertures 28 are suitably provided. As is known in the art, apertures 28 permit fluid to enter lumen 21 to facilitate drainage of fluids from the patient. Apertures 28 may be provided in body 24 of tube 12 in any conventional fashion such as by drilling, piercing, or the like.

Figure 5:
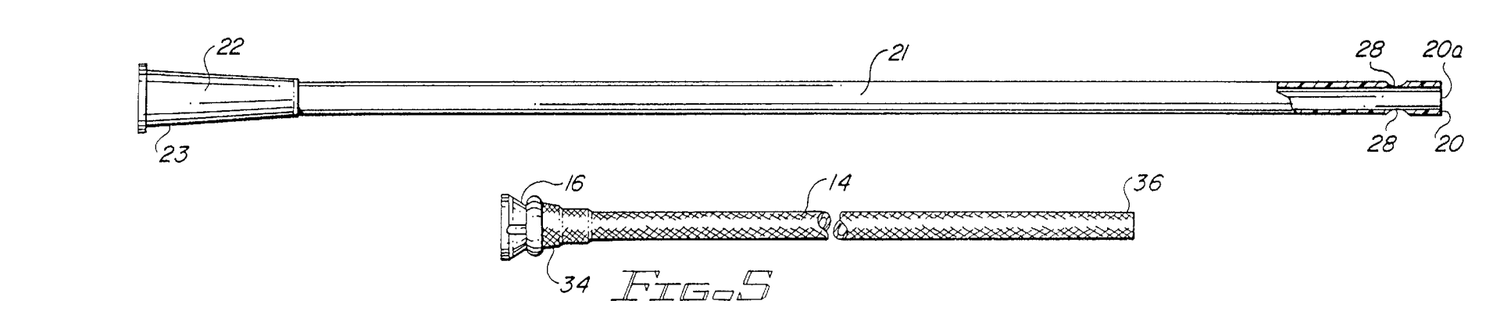
FIG. 5 is an elevational view of the catheter of FIG. 2 with the membrane removed therefrom and a urine bag adapter attached to the catheter tube.

Tube 12 is suitably configured at trailing edge 22 to be connected to a urine collection bag (not shown). For example, trailing edge 22 of tube 12 preferably includes a coupler 26 securely affixed thereto. Coupler 26 is suitably configured to facilitate adaption of tube 12 to the opening of a conventional urine collection bag or the like. As shown in FIG. 1, coupler 26 suitably comprises an enlarged portion of tube 12 proximate trailing edge 22. Alternatively, and with reference to FIG. 5 adapter 23 may be suitably attached to trailing edge 22 of tube 12 by any conventional means. While most conventional catheters, particularly urinary catheters, have a conventional adapter securely attached thereto when initially assembled, in accordance with a preferred aspect of the invention, adapter 23 preferably is not affixed to tube 12 until after catheter 10 is used, for example when tube 12 is inserted into the bladder of a patient. As the following discussion will make clear, in accordance with this aspect of the present invention, adapter 23 is preferably attached to tube 12 only after membrane 14 is removed therefrom, or when membrane 14 is desirably left in place only after catheter 10 is suitably inserted into the bladder of a patient.

As best seen in FIG. 1, tube 12 may have a diameter which varies from leading edge 20 to trailing edge 22. The diameter of tube 12 in the area of leading edge 20 is advantageously in the range of about 5 to about 6 mm, and may vary at increments of about 0.33 mm from leading edge 20 to trailing edge 22. Alternatively, and with momentary reference to FIG. 5, catheter tube 12 may be suitably configured to possess a uniform diameter about its length. In such case, adapter 23 (e.g., a conventional urine bag adapter or any other adapter) may be suitably attached to tube 12 to enable tube 12 to be suitably interconnected to other items such as a drainage collection bag, urine bag, etc.

Leading edge 20 of catheter 10 is preferably configured with an open end 20a (See, for example, FIG. 5) which communicates with lumen 21. As will be appreciated by those skilled in the art, this differs from most conventional catheters, such as conventional Foley catheters, which instead have a wholly or partially closed leading edge. Preferably, lumen 21 of tube 12 is configured to have a smooth configuration, most preferably having a radius in the range of 0.050 in. for a tube having a diameter of about 0.25 in. Leading edge 20 of tube 12 optionally may be comprised of a more rigid material than the remainder of tube 12. As explained in greater detail hereinafter, as catheter 10 is inserted into the patient, membrane 14 is caused to fold over and escape the interior of tube 12 about leading edge 20 of tube 12. Providing leading edge 20 with enhanced rigidity also tends to avoid dilation of leading edge 20, and may further facilitate the sliding between membrane 14 and tube 12.

The strength of catheter tubing together with the maximum size of lumen 21 are cooperative factors. For example, when catheter 10 is utilized in the form of a urinary catheter, it is desirable that tube 12 have an outer diameter in the range of about 0.20 in. to about 0.30 in., typically about 0.25 in. The diameter of lumen 21 of tube 12 is thus preferably in the range of about 0.10 in. to about 0.20 in. The particular material used should have sufficient strength such that tube 12 does not collapse upon itself during insertion, but also sufficient flexibility to permit maneuvering of catheter 10 during a catheterization procedure.

Tube 12 may also be provided with one or more enlargements or balloons (not shown) to enable catheter 10 to be maintained permanently in place inside the bladder. As is known in the art, such balloons or inflatable bags may be inflated when the catheter has been advanced to its desired position inside the bladder to ensure retention of the catheter in such position and prevent its accidental withdrawal.

Tube 12 generally can be formed in any conventional configuration. In accordance with one aspect of the invention, tube 12 has a generally circular configuration, as shown best in FIG. 6. Tube 12 preferably has a length characteristic of conventional catheters, tubes or probes. For example, when catheter 10 is used as a urinary catheter for males, it will generally have a length of from about 30 cm to about 50 cm, typically about 40 cm; when utilized as a urinary catheter for females, tube 12 generally will have a length of from about 15 cm to about 30 cm, typically about 20 cm.

Tube 12 preferably comprises a flexible polymeric material, for example an FDA certifiable material. In accordance with a preferred aspect of the invention, tube 12 comprises a polymeric material having a Shore A hardness in the range of about 55 durometer to about 160 durometer, and preferably about 60 durometer to about 90 durometer, and more preferably in the range of about 65 durometer to about 75 durometer. Suitable polymeric materials include thermoplastic polymers, for example polyurethanes, polyvinyl chlorides, or the like (e.g., medical grade polyvinyl chloride). Such thermoplastic polymers may be natural or synthetic, and may be modified or enhanced by the addition of lubricants such as glycerine, glycol and the like. Other conventional additives now known or hereafter devised by those skilled in the art also may be suitably included.

It should be understood that any material may be used to suitably form tube 12, and that the above examples are provided for illustration purposes only. A particularly preferred material for tube 12 is polyvinyl chloride (PVC) catheter tubing having a Shore A hardness in the range of about 75±5 durometer. The preferable PVC tube 12 can be provided in various diameters, primarily depending upon its use. As will be appreciated by those skilled in the art, tube 12 when used as a urinary catheter has a circumference of about 8 to about 24 French (and thus a corresponding diameter of about 2.5 to about 8.0 mm). As will be discussed in greater detail below, it has been found that tube 12, comprising PVC, works particularly well with the preferred PTFE membrane 14.

Membrane 14 preferably comprises a thin, flexible polymeric material advantageously having sufficient lubricity to smoothly slide out of and over leading edge 20 and subsequently slide back over the exterior of tube 12. It should be understood, however, that any suitable membrane material having sufficient strength, integrity, flexibility and lubricity may be utilized in accordance with the present invention to form membrane 14, provided the material has sufficient strength and flexibility to be medically acceptable when in use.

For example, while various combinations of materials for membrane 14 and tube 12 may be used in the context of the invention, it is important that the material and/or materials selected exhibit sufficient non-adhesiveness and/or anti-frictional characteristics such that the frictional force exerted by membrane 14 on the catheter tube 12 as membrane 14 is withdrawn therefrom is less than the frictional force exerted by catheter tube 12 on membrane 14. In accordance with a particularly preferred embodiment of the present invention, membrane 14 suitably comprises a material which can be advanced (i.e., withdrawn from tube 12) easily without the use of lubricants, hydraulics, pneumatic or mechanical assists. Stated another way, tube 12 and membrane 14 suitably are formed of materials which enable membrane 14 to be easily withdrawn from tube 12 in a "dry" state without the need for lubricants applied to either membrane 14 and/or tube 12.

More specifically, while various prior art catheter designs are known, these designs generally do not provide a catheter which is medically acceptable for use in vivo. As is demonstrated in Table 1 below, the various material combinations of known catheters simply do not work effectively.

TABLE 1

| CATHETER/SIZE | MEMBRANE/THICKNESS | RESULT |
| --- | --- | --- |
| PVC; 14 Fr | LDPE; 0.001 | Lock |
| PVC; 14 Fr | HDPE; 0.001 | Lock |
| PVC; 18 Fr | HDPE; 0.012 | Lock |
| PVC; 14 Fr | SLC; 0.004 | Lock |
| PVC; 14 Fr | Natural Latex; 0.006 | Lock |
| PVC; 14 Fr | Polyurethane; 0.002 | Unable to load |
| PVC; 14 Fr | Polyester; 0.001 | Lock |
| PVC; 14 Fr | Saran; 0.002 | Lock |
| PVC; 14 Fr | LDPE with fish line | Some advancement |
| PVC; 14 Fr | LDPE loaded with Starch; 0.002 | Some advancement; membrane breaks |
| 30–40 Durometer Latex; 14 Fr (Teflon coated tip) | PTFE; 0.001 | Lock |
| Polyurethane; 17 Fr | Latex; 0.006 | Lock |
| Teflon; 12 Fr | LLDPE; 0.001 | Lock |
| PVC; 14 Fr | LDPE; 0.095 | Lock |
| PTFE; 18 Fr | LDPE; 0.095 | Lock |
| PTFE; 18 Fr | HDPE; 0.012 | Lock |
| PTFE; 18 Fr | LDPE loaded with Starch; 0.002 | Some advancement |

As used in Table 1, the term "lock" refers to the situation where the forces exerted by the catheter on the membrane and/or by the membrane on the catheter are such that the membrane cannot be withdrawn from the catheter. Where some advancement of the membrane with respect to the catheter was observed, it is noted; even in such cases, however, the membrane was not easily removable from the catheter.

In contradistinction to the foregoing examples, a catheter in accordance with the present invention, preferably comprising tube 12 formed of PVC having a circumference in the range of 12 to 24 French and a polytetrafluoroethylene membrane 14 having a thickness in the range of less than about 0.004 in., preferably 0.0005 to about 0.0025 in. provides a medically acceptable catheter which is convenient to use. That is, unlike the material combinations set forth in Table 1, the combination of materials of catheter 10 in accordance with the present invention permit membrane 14 to be easily withdrawn from tube 12, thereby reducing the passage of infectious material and reducing trauma to the patient as catheter 10 is introduced.

Membrane 14 preferably comprises a substantially uniform cylindrical tube formed of a polytetrafluoroethylene resin, a modified PTFE resin, or combinations thereof. In accordance with a particularly preferred aspect of the present invention, membrane 14 is formed from a sintered PTFE film formed by skiving it off a billet to a thickness of less than 0.004 in., preferably on the order of about 0.001 in. The PTFE billet is preferably a modified PTFE, optimally either Hoechst TFM 1700 or TFM 1702 available from DeWall Industries of Saunderstown, R.I. under the names DW/200, and DW/220 respectively. Such material comprises a modified TFE polymer, modified by the addition of a small amount of perfluoro propyl vinyl ether (PPVE). It is believed that the addition of PPVE causes the PTFE to be more amorphous and more plasticized than pure crystalline PTFE. Such modification also permits the film to be heat sealed upon itself, (i.e., interfacial fusion).

It should be appreciated that other PTFE films may be suitably used as may be now known or hereafter devised by those skilled in the art. For example, PTFE homopolymers or copolymers with co-monomers like PPVE, PFA and the like may be suitably used. It is important, however, that the film be usable to form membrane 14 which when used in connection with tube 12 can be easily withdrawn, (i.e., does not "lock") when membrane 14 is withdrawn in a "dry" state.

In accordance with a further preferred aspect of the present invention, membrane 14 having multiple global sources may also comprise a modified PTFE resin available from DuPont under the name Mitsul-DuPont TG 70-J which has been sintered into billets, annealed, and skived to a thickness of 0.001 in.

Figures 6, 7, 8, 9, 10, 11:
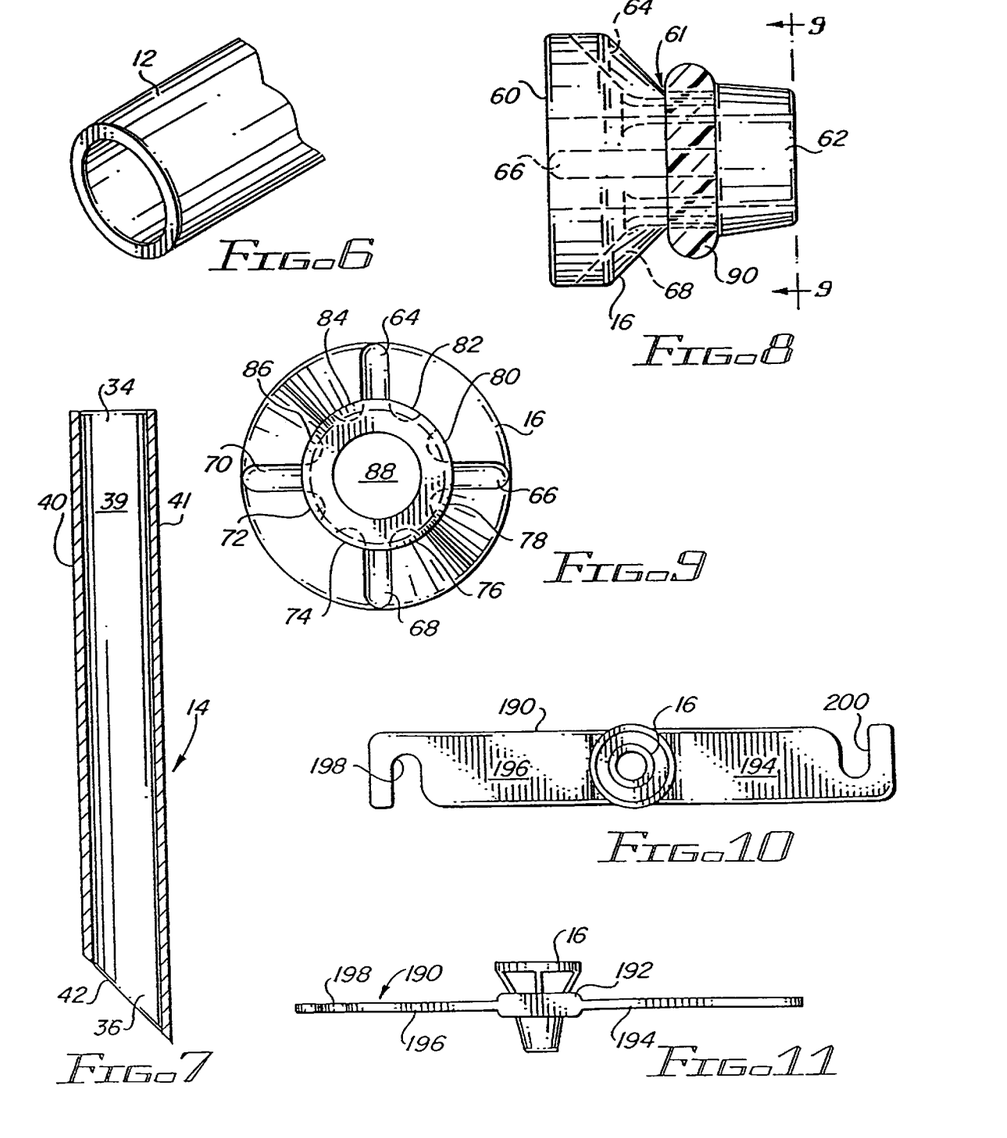
FIG. 6 is a sectioned perspective view showing one type of catheter tubing useful in accordance with the present invention.
FIG. 7 is an enlarged elevational view of a preferred membrane configuration useful in connection with the catheter in accordance with the present invention.
FIG. 8 is an enlarged side elevational view of a guide assembly useful in connection with the catheter of the present invention.
FIG. 9 is an end view of the guide assembly of FIG. 8 taken along the line 9—9 of FIG. 8.
FIG. 10 is an enlarged top plan view of an alternative embodiment of a guide ring assembly useful in connection with the catheter of the present invention.
FIG. 11 is an enlarged side elevational view of the guide ring assembly of FIG. 10.

As previously noted, membrane 14 preferably comprises a generally cylindrical tube, the walls of the tube preferably having a thickness of less than about 0.004 in., more preferably less than about 0.0025 in., and optimally less than about 0.001 in. It has been found that one way of forming such a tube is by joining together two (2) film layers one on top of the other. Specifically, and in accordance with a preferred aspect of the present invention, once films having a thickness of less than 0.004 in. are obtained, they are suitably arranged to form a tube. Preferably, two layers of the film are placed one on top of the other and the longitudinal edges thereof heat sealed. With reference to FIG. 7, membrane 14 preferably comprises two layers 39 which are heat sealed along the respective ends 40 and 41. Preferably, ends 40 and 41 are heat sealed in a conventional manner; for example heat sealing may be accomplished through use of heat sealing bars. When catheter tube 12 possesses a diameter of about 14 French, the film used to make membrane 14 preferably is on the order of about 0.75 in., and the seals on the order of about 0.125 in. such that the distance between the seals is on the order of about 0.5625 in. Once edges 40 and 41 of membrane 14 are suitably sealed, excess material is trimmed, and the tubes are generally cut into lengths of about 8 to 15 cm, optimally about 10 cm.

To improve the strength and flexibility of membrane 14, it is preferable that membrane 14 is suitably tensilized. As those skilled in the art will appreciate, tensilizing of polymeric films can be accomplished in a variety of ways. In accordance with the present invention, tensilizing can be accomplished through any conventional or hereafter devised method. It has been found, for example, that simply working the membrane formed of a sintered PTFE film, such as in one's fingers, provides a modicum of flexibility and improved strength, as may other tensilizing devices such as pin rollers and the like. A tensilizing fixture such as that shown in FIG. 15 may also be employed. In accordance with a preferred aspect of the present invention, film 14 is preferably elongated from about 25 to about 300 percent, more preferably from about 50 to about 200 percent, and optimally from about 125 to 150 percent.

Figure 15:
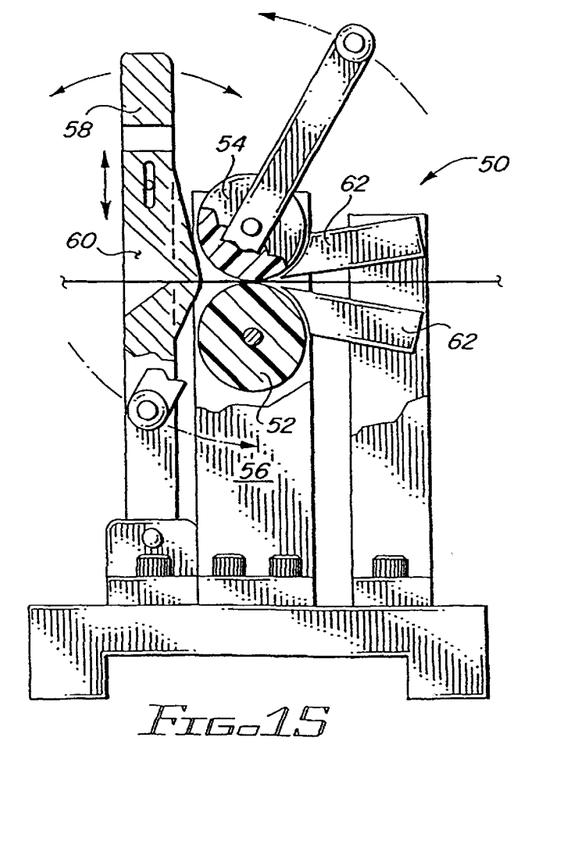
FIG. 15 is a schematic view of a fixture useful in strengthening the membrane film useful in connection with the catheter of the present invention.

With reference to FIG. 15, membrane film 14 can be elongated through use of fixture 50 comprising respective rollers 52 and 54 suitably attached to a frame 56. Preferably, rollers 52 and 54 are interference fit and under a load, (e.g. about 50 pounds each). A handle 58 is operable to cause movement of rollers 52 and 54 to thereby draw membrane 14 therethrough. Preferably, concurrently with the advancement of membrane 14, a force is applied to trailing edge 36 to suitably elongate membrane 14. Such force may be applied manually or through mechanical assist.

As shown in FIG. 15, rollers 52 and 54 define an inlet 60 and an outlet 62. Membrane 14 is preferably fed through fixture 50 at inlet 60 such that film 14 is advanced forward while simultaneously being clamped and pulled backward at an appropriate force and rate. As film 14 is advanced between rollers 52 and 54, it extends through outlet 62. Preferably, leading edge 34 of membrane 14 is not tensilized. In particular, the portion of leading edge 34 which is to be attached to guide ring 16 preferably is not tensilized; it has been found that in such a state it has greater axial strength and, thus, can be more easily sized and ultimately attached to guide ring 16. To that end, preferably, leading edge 34 is fed through rollers 52 and 54 and no pressure is exerted on leading edge 34.

It should be appreciated that, while fixture 50 is preferably used in accordance with the present invention, film 14 can be tensilized in accordance with any method now known or hereafter devised by those skilled in the art. In particular, it should be appreciated that film 14 can be tensilized by hand or through use of other manual or automatic mechanisms. It will be appreciated by those skilled in the art that tensilizing in this manner is useful to longitudinally strengthen the membrane film and lower its frictional coefficient through coldflow molecular orientation of the membrane film.

As briefly noted above, it has been found that a tensilized membrane 14 comprising sintered, modified PTFE film having a thickness of less than about 0.004 mm can be effectively used in connection with a standard PVC catheter tube 12 to obtain medically acceptable results. As will be discussed in greater detail below, preliminary clinical studies using catheter 10 in accordance with the present invention have yielded surprising and unexpected results.

Once suitably formed, membrane 14 is preferably suitably attached to guide ring 16. With reference to FIG. 1, guide ring 16 may suitably comprise an enlarged portion optimally configured to fit over the glans of a male patient during insertion of catheter 10. When catheter 10 is used as a urinary catheter for males, for example, enlarged portion 37 is suitably configured to facilitate holding membrane 14 firmly in place over the glans of the penis during insertion of the catheter.

If it is desired to manually grasp end 34 of membrane 14 while the catheter is in place, guide ring 16 may be suitably configured to permit the user to grasp guide ring 16. With particular reference to FIGS. 8 and 9, guide ring 16 may alternately be configured to possess a nipple configuration. In accordance with this embodiment, guide ring 16 is suitably configured to include a grip portion 60, a membrane receiving portion 62, and a ribbed body spanning therebetween. Guide ring 16 further includes a central lumen 88 through which membrane 14 is fed. With continued reference to FIGS. 8 and 9, a plurality of ribs 64, 66, 68, and 70 are preferably equidistantly spaced about the circumference of grip portion 60. Suitably arranged between ribs 64–70 are a plurality of sterilization apertures 72, 74, 76, 78, 80, 82, 84, and 86. Guide ring 16 is suitably configured such that membrane 14 is received at receiving portion (nipple) 62. The outer diameter of attaching portion 62 is preferably sufficiently larger than the inner diameter of membrane 14 such that a "force-fit" engagement between membrane 14 and guide ring 16 is maintained. Optional adhesives may be utilized with suitable surface changes, but in general are unnecessary to ensure secure attachment of membrane 14 to guide ring 16. Snap ring 90 is suitably placed over nipple 62 and is force fit to hold membrane 14 snugly in membrane-receiving area 61.

Figure 12:
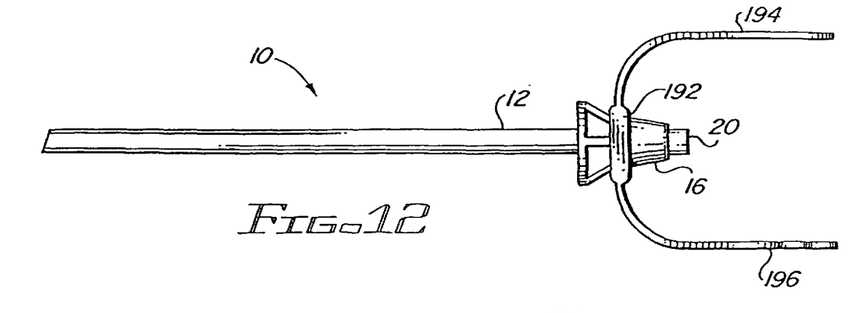
FIG. 12 is an enlarged side elevational view of the guide ring assembly of FIGS. 10 and 11 positioned in connection with a catheter in accordance with the present invention showing the wings thereof in an extended position.
Figure 13:
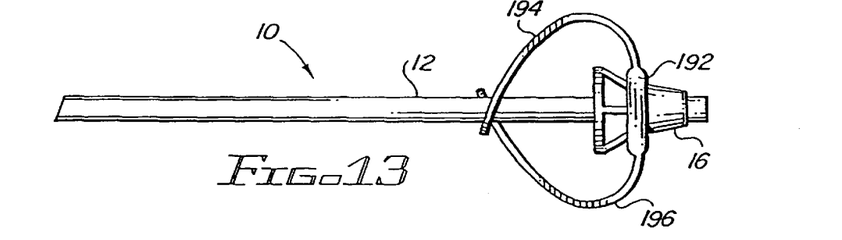
FIG. 13 is an enlarged elevational view of the catheter assembly of FIG. 12 showing the wings of the guide ring assembly attached to the catheter tube.

In accordance with a further embodiment of the present invention, and with reference to FIGS. 10–13, guide ring 16 may be used in connection with a snap ring 190 which is configured to orient the glans of a male patient during insertion of a catheter. In this regard, it has been found that catheter 10 according to the present invention is most easily inserted into a male patient when the male patient's penis is held stationary with respect to leading edge 20 of catheter 10. To this end, and with reference to FIGS. 10 and 11, snap ring 190 which is suitably used in connection with guide ring 16 includes a central ring 192 and respective wings 194 and 196. As shown best in FIG. 11, wings 194 and 196 extend laterally from ring 192, and with reference to FIGS. 12 and 13 are flexibly movable to a variety of convenient positions. In particular, and with specific reference to FIGS. 12 and 13, wings 194 and 196 are suitably configured to be arranged in a U-shape with respect to leading edge 20 of catheter 10. In such a position, wings 194 and 196 serve to orient the penis with respect to catheter 10 and provide for easy insertion thereof. Upon insertion or at any time thereafter, wings 194 and 196 are suitably configured to be conveniently attached to tube 12 so that they are not in the way of further maneuvering of catheter 10. In this regard, and with reference to FIGS. 10 and 13, wings 194 and 196 are suitably provided with respective catheter receiving apertures 198 and 200. As shown in FIG. 10, apertures 198 and 200 may comprise generally U-shaped cutouts in wings 194 and 196. As shown in FIG. 13, apertures 198 and 200 enable wings 194 and 196 to be suitably attached to tube 12 of catheter 10.

Snap rings 90 and 190 may be comprised of any suitable material but preferably comprise polymeric material having sufficient rigidity while at the same time sufficient flexibility to fit over and snap onto guide ring 16. In connection with snap ring 190, wings 194 may be suitably comprised of the same or similar material and optionally may be enforced with suitable flexible rigidifying members. For example, wings 194 and 196 may comprise a metallic inner member which is surrounded by a polymeric outer member, the metallic inner member having sufficient flexibility while at the same time being able to maintain wings 194 in either their open (see FIG. 12) or closed (see FIG. 13) positions. Preferably, rings 190 and 192 are formed from a polyurethane resin having a Shore A hardness in the range of about 90 durometer.

Guide ring 16 may comprise any suitable material such as metal, plastic or the like. Guide ring 16 suitably comprises a material having a relatively low frictional coefficient, such as polyethylene-based materials. Irrespective of the particular material used for guide ring 16, the inner bearing surface thereof optimally exhibits sufficient lubricity to permit easy passage along the outside of tube 12 during use.

As will be appreciated, the respective sizes of guide ring 16 and membrane 14 may be chosen to facilitate their convenient movement over the exterior surface of tube 12. For example, if the diameter of tube 12 at leading edge 20 is in the range of about 5 mm, then the diameter of membrane 14 and the inner diameter of guide ring 16 in accordance with one aspect of the invention should be at least about 6 mm.

Once membrane 14 is suitably prepared, as described above, it is inserted (loaded) into and fixedly attached to guide ring 16. Specifically, and in accordance with a particularly preferred aspect of the present invention, membrane 14 is first threaded through lumen 88 of guide ring 16. Leading edge 34 of membrane 14 is opened, such as by rolling the flat tube section to produce an opening. Once edge 34 is opened, edge 34 is then placed onto nipple 62. As shown in FIG. 8, surface 62 is preferably tapered from its leading edge to retainer receiving area 61. Preferably, the open leading edge 34 is inserted onto nipple 62 through use of an air jet which also is configured with a tapered nipple. Specifically, the nipple of the air jet is first placed into leading edge 34; as air is blown into the body of membrane 14, it opens. Air is then preferably blown towards the outermost edge of leading edge 34, thereby causing edge 34 to invert and fold back over nipple 62. If desired, a cylindrical sleeve (not shown) configured to ride over the tapered nipple 62 can be used to further advance edge 34 reasonably over nipple 62, such that edge 34 is well within retaining area 61. Snap ring 90 is thereafter placed onto guide ring 16. Snap ring 90 suitably rides up over the cone front of nipple 62 of guide ring 16 and snaps back into the smaller central shaft area 61, thus trapping the film therebetween.

Once membrane 14 is suitably attached to guide ring 16, membrane 14 is preferably trimmed to an appropriate length and trailing edge 36 suitably angled, such as is shown best in FIG. 7. Preferably, membrane 14 is trimmed to an operational length of between about 6 and about 12 cm, more preferably about 8 cm. Membrane 14 typically exhibits a length less than that of tube 12. For example, when catheter 10 is used as a urinary catheter, membrane 14 is desirably in the range of about 10 to about 40 cm, and preferably about 8 to about 15 cm in length. Additionally, trailing edge 36 is preferably trimmed so that it has an angular taper of between about 30 and about 60 degrees, optimally about 45 degrees. It has been found that this taper aids in the removal of membrane 14 from tube 12, likely by reducing the drop-off of pressure when membrane 14 is fully inverted and catheter tube 12 continues being inserted into the anatomical canal of the patient.

The assembly comprising membrane 14 and guide ring 16 is thereafter loaded into tube 12 and catheter 10 is thereafter sterilized for use, such as for use as a urinary catheter. While membrane 14 attached to guide ring 16 can be loaded into tube 12 in any suitable manner, preferably a loading device (not shown) may be suitably inserted through lumen 21 of catheter tube 12, which loading device can be used to grab trailing edge 36 of membrane 14 and pull it down through lumen 21 towards trailing edge 22 of tube 12.

Figure 2:
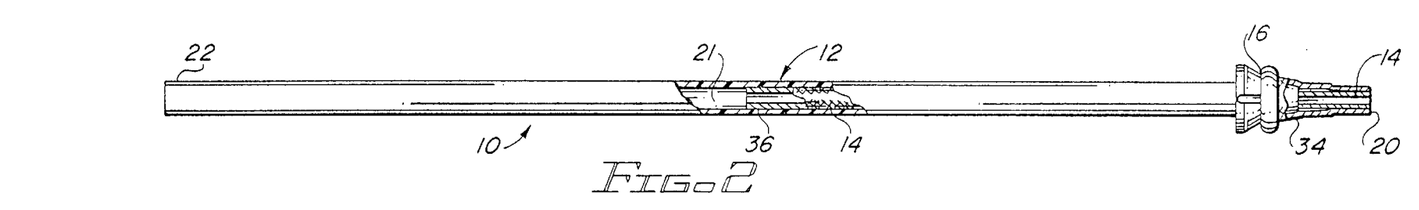
FIG. 2 is a side elevational view of a further preferred embodiment of a catheter in accordance with the present invention.
Figure 3:
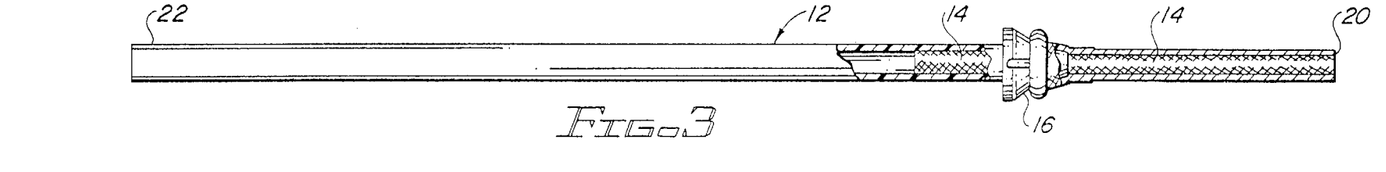
FIG. 3 is an elevational view of the catheter of FIG. 2 upon insertion into a patient, such as insertion into the patient's urethral canal.
Figure 4:
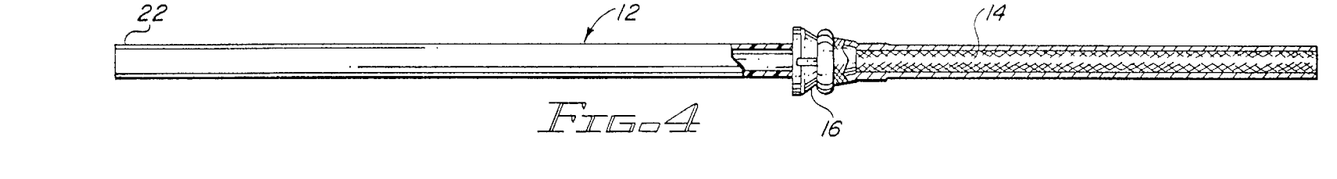
FIG. 4 is an elevational view of the catheter of FIG. 2 upon further insertion into the cavity.
Figure 14:
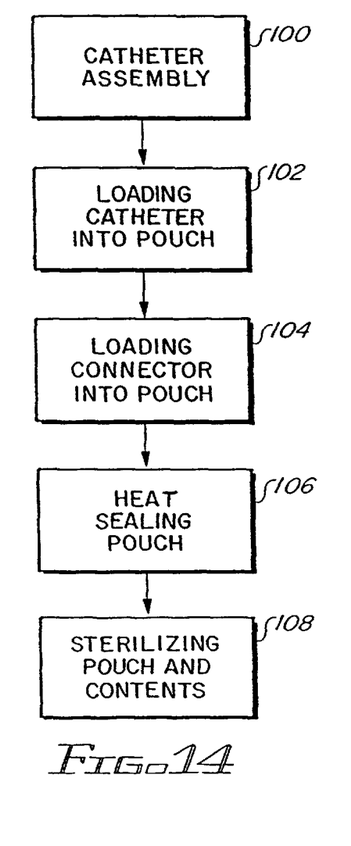
FIG. 14 is a flow chart illustrating the steps of a sterilization method useful in sterilizing a catheter in accordance with the present invention.

With reference now to FIG. 2, once membrane 14 is suitably loaded (snug) within tube 12, guide ring 16 is located near leading edge 20 of tube 12, with the majority of membrane 14 contained within lumen 21 of tube 12. To ensure the safety of use of catheter 10, it is essential that loaded catheter 10 be appropriately sterilized. To that end, and with reference to FIG. 14, catheter assembly 10 is loaded into a conventional Chevron pouch having a dimension of about 20×3 in. with the leading edge first. Connector 23 is thereafter dropped into the pouch, and the pouch is sealed. With specific reference to FIG. 14, step 100 relates to assembly of the catheter in the manner described herein. Step 102 involves the loading of catheter assembly 10 into a pouch. Step 104 requires loading of connector 23 into the pouch. Step 106 involves heat sealing of the pouch with catheter assembly 10 and connector 23 suitably contained therein. In accordance with step 106, conventional heat sealing methods can be employed. Finally, the pouch with its contents is, as indicated at step 108, suitably sterilized such as through the use of ethylene oxide. In accordance with conventional sterilization procedures, the pouch is first exposed to ethylene oxide and then oxygen, and multiple exposures are cycled over predetermined periods of time.

The preferred configuration of guide ring 16 is particularly helpful in connection with the sterilization process, because apertures 72–86 enable the sterilizing gas to permeate the entirety of the device. Specifically, the intimate area of contact between membrane 14, snap ring 90, and guide ring 16 can be readily sterilized due to the presence of troughs 72–86.

A plurality of calibrations 170, (i.e. one or more lines), may be suitably imprinted on the exterior surface of tube 12. Similarly, a plurality of calibrations 172, (i.e. one or more lines), may be suitably imprinted on the interior surface of membrane 14. The cooperation of calibrations 170 and 172 enable the user to determine the position of second end 36 of membrane 14 as catheter 10 is inserted into a body cavity.

Referring now to FIGS. 1–5, membrane 14 is advantageously disposed, prior to insertion of the catheter into the patient, such that substantially all of membrane 14 is contained within lumen 21, with the exception of first end 34 which engages guide ring 16. As briefly noted above, during assembly of catheter 10, membrane 14 is inserted into tube 12 in a suitable manner. For example, membrane 14 may be threaded through lumen 21 of tube 12. Alternatively, membrane 14 may be pneumatically or hydraulically inflated to facilitate guiding the membrane through tube 12. Guide ring 16 is initially disposed exteriorly of tube 12 about the exterior of leading edge 20 of tube 12 (see, e.g., FIG. 1). Prior to use, guide ring 16 and first end 34 are pulled back over leading edge 20 of tube 12, as shown for example in FIG. 2. As will be discussed more fully in connection with FIGS. 2–5, during the catheterization procedure using catheter 10, second end 36 of membrane 14 travels through lumen 21 towards leading edge 20 of tube 12 and is desirably drawn completely through leading edge 20, such that membrane 14 is turned completely inside-out and circumscribes tube 12.

With continued reference to FIGS. 2–5, the operation of an exemplary embodiment of the present invention will now be described. As best seen in FIG. 2, catheter 10 is initially assembled such that membrane second end 36 is disposed within tube 12. Membrane first end 34 of membrane 14 is affixed to guide ring 16 and is positioned proximate to the leading edge 20 of tube 12. Thereafter, guide ring 16 is urged back over leading edge 20 to initiate the unfolding of membrane 14 over tube 12, as shown in FIG. 2. That is, the portion of membrane 14 external to tube 12 is turned inside-out such that as it is pulled back (to the left in FIGS. 2–4) along the length of tube 12; the "folded over" portion of membrane 14 circumscribes tube 12. Catheter 10 is now ready for insertion into a patient.

Insertion of catheter 10 may be accomplished through the use of known catheterization techniques. For example, when using catheter 10 in the catheterization of a male's bladder, the patient (or the attending medical personnel) holds guide ring 16 firmly in place over the male's penis, with one hand. Alternatively, and with reference to FIG. 12, through use of snap ring 192, wings 194 and 196, as previously noted, can be suitably arranged to hold the male's penis in place with respect to the leading edge 20 of catheter 10. In any event, the other hand is used to introduce catheter 10 into the urethral canal by pushing it inside the urethral canal. In particular, tube 12 is grasped and manually urged into the urethral canal thereby causing membrane 14 to begin to fold back over tube 12 in an inside-out fashion. Further pushing of tube 12 into the urethral canal results in continued extraction of membrane 14 from tube 12 (see FIGS. 3 and 4). As membrane 14 is drawn out of tube 12, it is interposed between tube 12 and the walls of the urethral canal, thereby preventing tube 12 from contacting the urethral mucosa and/or the walls of the urethral canal for the length of membrane 14. Consequently, tube 12 does not urge infectious matter from the lower urinary tract up into the upper urinary tract and/or the bladder as tube 12 travels to the bladder to facilitate voiding.

In accordance with an optional feature of the present invention, the user can monitor the degree of insertion of catheter 10, as well as the location of membrane 14, by visual inspection of calibrations 170 of tube 12 in conjunction with calibrations 172 of membrane 14.

In any event, once tube 12 has reached the bladder, membrane 14 may be extracted by grasping guide ring 16 and pulling membrane 14 rearwardly until second end 36 of membrane 14 is completely removed from the patient. (See FIG. 5). After membrane 14 is removed, tube 12 remains in place and is suitably situated to permit voiding of urine from the bladder. Alternatively, membrane 14 may be left in place for a period of time or throughout the catheterization process. In the event membrane 14 is removed, membrane 14 attached to guide ring 16 is thereafter discarded. The removal of membrane 14 may be beneficial; as membrane 14 is removed, it may act as a unidirectional brush which aids in the cleansing of pathogens contained within the urethral canal. That is, as membrane 14 is pulled back and removed from the urethral canal, a wiping action occurs such that pathogens contained within the canal tend to be attracted to and moved outwardly from the urethral canal.

Once tube 12 is suitably inserted into the patient's bladder and membrane 14 removed therefrom or maintained in place, adapter 23 can be suitably attached to trailing edge 22 of tube 12 and ultimately to a urine collection bag.

It should thus be appreciated that catheter 10 in accordance with the present invention enables a tube or probe to be inserted into an orifice, such as the urethral canal, without transporting pathogens or bacteria normally inhabitant at or near the glans or in the proximity of the lower urethral canal to the bladder, through the use of non-contaminating membrane 14.

Preliminary clinical studies using catheter 10 in accordance with the present invention have revealed the surprising and unexpected results set forth in Table 2 below. In accordance with these studies, three tests have been performed. The first test was conducted on a group of 27 male patients suffering from vesical papillomatosis and treated with Farmorubicina or Interferon by endovesical instillation who underwent intermittent catheterization of the bladder with traditional catheters. A second group of 27 similar patients were treated with catheter 10 in accordance with the present invention. A third group of four patients who had a positive urine culture after traditional catheterization despite ongoing antibiotic treatment were later catheterized with catheter 10 in accordance with the present invention. Such patients with concurrent metabolic disorders (e.g., diabetes) are at high risk for recurrent urinary tract infections. All catheters were sterilized prior to use. A routine urine culture was obtained 48 to 72 hours after completing catheterization of the bladder. In particular, a sample of urine (midstream) was obtained for a culture, pathogen count and possible identification. The urine samples were then evaluated. The results of these tests are listed below in Table 2.

TABLE 2

| TEST | NUMBER OF PATIENTS | NATURE OF URINE CULTURE | BACTERIAL COUNT | RATE OF UTI |
|---|---|---|---|---|
| 1 | 27 | Positive urine culture | Greater than 100,000/ milliliter of urine | 5 of 27 18.5% |
| 2 | 27 | Negative urine culture | Less than 100,000/ milliliter of urine | 0 out of 27 0% |
| 3 | 4 | Negative urine culture | Less than 100,000/ milliliter of urine | 0 out of 27 0% |

These results support the surprising performance of catheter 10 in accordance with the present invention. In particular, these results evidence that the unique combination of membrane 14 formed of a modified polytetrafluoroethylene resin and a polyvinyl chloride catheter tube 12 is useful in preventing urinary tract infection, even in high-risk patients.

Those skilled in the art will also appreciate that catheter 10 of the present invention, in addition to its usefulness in catheterization procedures, can be utilized as a probe for other known or hereafter devised medical techniques. For example, the probe of the present invention can be used for the drainage of internal fluids. Further, catheter 10 may be used to perform bladder lavages in continuum by injecting large amounts of fluids (e.g., water) into the bladder via catheter 10. For example, once catheter 10 is completely inserted and membrane 14 inverted such that end 36 is proximate leading edge 20, fluid may be injected into the area between membrane 14 and the exterior surface of tube 12, thus causing membrane 14 to expand slightly. The fluid entering and cleansing the bladder can then be extracted through lumen 21 of tube 12.

It will be understood that the above description is of preferred exemplary embodiments of the present invention, and that the invention is not limited to the specific forms shown and described herein. For example, some or all of the components may be plasma surface-treated to enhance hydrofilasticity. Further, various alternative configurations of catheter 10, particularly tube 12, may be readily incorporated by those skilled in the art. These and other modifications may be made in the design and arrangement of the elements within the scope of the invention, as expressed in the appended claims.

We claim:

1. An improved catheter including:
   (a) a polyvinyl chloride catheter tube having a diameter in the range of about 8 to about 24 French, said catheter tube having first and second open ends and a lumen spanning therebetween;
   (b) a membrane formed of a modified polytetrafluoroethylene (PTFE) resin, said membrane having a thickness of between about 0.0005 and about 0.0025 in., said membrane comprising a skived film from a sintered PTFE billet having heat sealed edges forming an elongated tube, and a tensilized elongated tube, said tube being elongated on the order of between about 100 and 150 percent; and
   (c) a means for advancing said membrane uniformly from said lumen of said catheter tube, a portion of said membrane being attached to said advancing means.

2. An improved catheter including:
   (a) a catheter tube having first and second open ends and an axial lumen spanning therebetween;
   (b) a perfluoropropylvinylether modified polytetrafluoroethylene (PTFE) resin membrane, said membrane having edges and a thickness; and
   (c) a guide, a portion of said membrane attached to said guide, wherein said guide is external to said axial lumen.

3. A tube assembly for insertion into an anatomical canal, the assembly comprising: a hollow tube having first and second ends and an axial lumen spanning therebetween;
   a guide comprising a first part for passing over said catheter, and a second part engageable with said first part to form a fit therebetween;
   a membrane comprising a perfluoropropylvinylether modified polytetrafluoroethylene resin having a first end, a second end, and a sealed generally tubular body spanning therebetween, said first end of said membrane attached to said guide such that said membrane is interposed between said first and second guide parts.

4. A catheter for aiding in the prevention of the passage of infectious material when inserted into an anatomical canal, said catheter comprising:
   a hollow catheter tube having first and second open ends;
   a membrane comprising a sintered, tensilized, perfluoropropylvinylether modified polytetrafluoroethylene resin wherein said membrane is generally tubular and is disposed within said catheter tube and is suitably removed from said first open end of said catheter tube such that said membrane is interposed between said catheter and said anatomical canal as said catheter is inserted into said anatomical canal.

* * * * *